US007169954B2

(12) United States Patent  
Mizuno et al.

(10) Patent No.: US 7,169,954 B2  
(45) Date of Patent: Jan. 30, 2007

(54) METHOD FOR PREPARING RUTHENIUM-CARRYING ALUMINA AND METHOD FOR OXIDIZING ALCOHOL

(75) Inventors: Noritaka Mizuno, Nerima-ku (JP); Kazuya Yamaguchi, Bunkyo-ku (JP); Hajime Ishida, Niihama (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 10/481,755

(22) PCT Filed: Apr. 25, 2003

(86) PCT No.: PCT/JP03/05299

§ 371 (c)(1),
(2), (4) Date: Dec. 23, 2003

(87) PCT Pub. No.: WO03/090926

PCT Pub. Date: Nov. 6, 2003

(65) Prior Publication Data

US 2004/0204597 A1 Oct. 14, 2004

(30) Foreign Application Priority Data

Apr. 26, 2002 (JP) ............................. 2002-126189  
Nov. 28, 2002 (JP) ............................. 2002-345108

(51) Int. Cl.
*C07C 45/29* (2006.01)  
*C07C 51/12* (2006.01)  
*C07C 51/16* (2006.01)

(52) U.S. Cl. ..................... 568/357; 568/361; 568/399; 568/402; 568/471; 562/519; 562/538

(58) Field of Classification Search ............... 568/357, 568/361, 399, 402, 471; 562/519, 538  
See application file for complete search history.

(56) References Cited

U.S. PATENT DOCUMENTS

| | | | |
|---|---|---|---|
| 3,673,257 A | 6/1972 | Di Bella | |
| 4,026,950 A | 5/1977 | Le Ludec | |
| 4,218,401 A | 8/1980 | Wymore | |
| 4,996,007 A | 2/1991 | Chao et al. | |
| 5,274,187 A | 12/1993 | Kimura et al. | |
| 6,166,264 A | 12/2000 | Ishii et al. | |
| 6,476,260 B1 | 11/2002 | Herrmann et al. | |

FOREIGN PATENT DOCUMENTS

| | | | |
|---|---|---|---|
| EP | 1078908 | A1 | 2/2001 |
| JP | 54-94491 | A | 7/1979 |
| JP | 57-108035 | A | 7/1982 |
| JP | 62-265244 | A | 11/1987 |
| JP | 1-130734 | A | 5/1989 |
| JP | 130734 | | 5/1989 |
| JP | 10-024235 | A | 1/1998 |
| JP | 10-137587 | A | 5/1998 |
| JP | 10-251188 | A | 9/1998 |
| JP | 2000-70723 | A | 3/2000 |
| JP | 2000-86245 | A | 3/2000 |
| JP | 2001-48824 | A | 2/2001 |
| JP | 2001-64222 | A | 3/2001 |
| JP | 2001-246262 | A | 9/2001 |
| JP | 2001-302581 | A | 10/2001 |
| JP | 3345943 | B2 | 9/2002 |
| SU | 978909 | A | 12/1982 |

OTHER PUBLICATIONS

Masaki Hashimoto et al., "Rutheniumalumina ni yoru Bunshi-jo Sanso o Sankazai to suru Benzyl Alcohol no Sanka Hanno", Shokubai Toronkai, Toronkai A, Yokoshu, Sep. 10, 2002, vol. 90, p. 165.

Kazuya Yamaguchi et al., "Ru/$Al_2O_3$ Shokubai o Mochiita Bunshi-jo Sanso o Sankazai to suru Alcohol-riu no Sentaku Sanka Hanno", Shokubai, Mar. 10, 2003, vol. 45, No. 2, pp. 157-159.

Kazuya Yamaguchi et al., "Supported Ruthenium Catalyst for the Heterogeneous Oxidation of Alcohols with Molecular Oxygen", *Angew. Chem. Int. Ed.*, vol. 41, No. 23, pp. 4538-4542.

F. Vocanson et al., "Dioxygen Oxidation of Alcohols and Aldehydes Over a Cerium Dioxide-Ruthenium System", *Synthetic Communications*, vol. 28, No. 14, 1998, pp. 2577-282.

K. Yamaguchi et al., "Creation of Monomeric Ru Species on the Surface of Hydroxyapatite as an Efficient Heterogeneous Catalyst for Aerobic Alcohol Oxidation", *J. Am. Chem. Soc.*, vol. 122, 2000, pp. 7144-7145.

K. Kaneda et al., "Heterogeneous Oxidation of Allylic and Benzylic Alcohols Catalyzed by Ru-Al-Mg Hydrotalcites in the Presence of Molecular Oxygen", *J. Org. Chem.*, vol. 63, 1998, pp. 1750-1751.

T. Matsushita et al., "Highly efficient oxidation of alcohols and aromatic compounds catalysed by the Ru-Co-Al hydrotalcite in the presence of molecular oxygen", *Chem. Commun.*, 1999, pp. 265-266.

Primary Examiner—Sikarl A. Witherspoon  
(74) Attorney, Agent, or Firm—Sughrue Mion, PLLC

(57) ABSTRACT

A ruthenium-carrying alumina, which is prepared by suspending alumina in a solution containing trivalent ruthenium and adding a base to the suspension, is provided. This ruthenium-carrying alumina is useful as a catalyst for oxidizing alcohols by contacting the alcohols with molecular oxygen, and can be used for oxidizing the alcohols at a high conversion to produce ketones, aldehydes, carboxylic acids, etc. with good productivity.

5 Claims, No Drawings

METHOD FOR PREPARING RUTHENIUM-CARRYING ALUMINA AND METHOD FOR OXIDIZING ALCOHOL

FIELD OF THE INVENTION

The present invention relates to a process for preparing a ruthenium-carrying alumina, and a process for producing ketones, aldehydes, carboxylic acids and the like by oxidizing alcohols with molecular oxygen in the presence of a ruthenium-carrying alumina as a catalyst.

PRIOR ART

As a process for oxidizing alcohols, a process of contacting the alcohols with molecular oxygen in the presence of a ruthenium catalyst is known. For example, U.S. Pat. No. 4,996,007 proposes to carry out the above oxidation reaction in the presence of a ruthenium catalyst such as a ruthenium-carrying alumina, a ruthenium-carrying carbon, etc. together with an oxygen-activator such as dihydrodihydroxynaphthalene. JP-A-11-226417 proposes to carry out the above oxidation reaction in the presence of a ruthenium catalyst such as dichlorotris-(triphenylphosphine)ruthenium, tetrapropylammonium perruthenate salt, a ruthenium-carrying carbon, etc. together with dioxybenzenes or their oxidized derivatives. Furthermore, JP-A-2000-70723 proposes to carry out the above oxidation reaction in the presence of a ruthenium-containing hydrotalcite.

However, the ruthenium catalysts used in the above conventional processes do not necessarily have sufficient catalytic activities so that the desired conversion of the alcohols is not achieved. Therefore, the conventional processes may not be satisfactory in the productivity of oxidized products.

SUMMARY OF THE INVENTION

One object of the present invention is to provide a process for preparing a ruthenium catalyst having a good activity to oxidize alcohols.

Another object of the present invention is to provide a process for preparing ketones, aldehydes, carboxylic acids and the like at a high productivity by oxidizing alcohols at a high conversion using a catalyst prepared by the process described above.

Accordingly, the present invention provides a process for preparing a ruthenium-carrying alumina comprising the steps of suspending alumina in a solution containing trivalent ruthenium and adding a base to the suspension, and a process for oxidizing an alcohol comprising the step of contacting the alcohol with molecular oxygen in the presence of a ruthenium-carrying alumina prepared by the process described above. Furthermore, the present invention provides a process for preparing a carbonyl compound comprising oxidizing an alcohol by the oxidizing process described above.

DETAILED DESCRIPTION OF THE INVENTION

In the process for preparing a ruthenium-carrying alumina according to the present invention, trivalent ruthenium (ruthenium(III)) is utilized as a ruthenium source, and alumina is suspended in a solution containing trivalent ruthenium.

Examples of ruthenium compounds which can be used as sources of trivalent ruthenium include ruthenium halides such as ruthenium(III) chloride, ruthenium(III) bromide, etc.; oxo acid salts such as ruthenium(III) nitrate, ruthenium (III) sulfate, etc.; and so on. They may be used as a mixture of two or more of them, if desired. Among them, ruthenium halides such as ruthenium(III) chloride are preferable.

Water is usually used as a solvent of the ruthenium solution, although a mixed solvent of water and an organic solvent, or an organic solvent alone may be used, if necessary. The amount of the solvent is adjusted such that a ruthenium concentration in the solution is usually from 0.1 mM to 1 M, preferably from 1 mM to 100 mM.

The kind of alumina to be suspended in the ruthenium solution is not limited, and various kinds of alumina such as α-alumina, β-alumina, γ-alumina, etc. may be used. Among them, γ-alumina is preferably used. The amount of alumina is adjusted such that an ruthenium content in the ruthenium-carrying alumina is usually from 0.1 to 20% by weight, preferably from 0.5 to 10% by weight.

Then, a base is added to the suspension of alumina prepared in the previous step to adjust the pH of the suspension to usually at least 8, preferably at least 10, more preferably 12 to 14. If no base is added, the activity of the ruthenium-carrying alumina as a catalyst for oxidizing alcohols is not sufficiently high.

Examples of the base include metal hydroxides such as sodium hydroxide, potassium hydroxide, magnesium hydroxide, etc.; metal carbonates such as sodium carbonate, potassium carbonate, magnesium carbonate, etc.; metal acetates such as sodium acetate, potassium acetate, etc.; ammonia; and the like. They may be used as a mixture of two or more of them, if desired.

After the addition of the base, the suspension is subjected to solid-liquid separation treatment. Thereby, the ruthenium-carrying alumina is recovered from the suspension. The solid-liquid separation treatment is usually filtration or decantation. The recovered ruthenium-carrying alumina may optionally be post-treated such as washing with water, drying, etc.

The ruthenium-carrying alumina prepared by the above process is preferably used as a catalyst for oxidizing an alcohol with molecular oxygen. This oxidation reaction may be carried out either in a liquid phase or in a gas phase. Preferably, it is carried out in the liquid phase.

The amount of the ruthenium-carrying alumina used in the oxidizing process is usually from 0.000001 to 1 mole, preferably from 0.0001 to 0.1 mole, more preferably from 0.001 to 0.05 mole, in terms of ruthenium per one mole of the alcohol.

The alcohol as a substrate to be oxidized may be a primary alcohol or a secondary alcohol, and may be a monohydric alcohol or a polyhydric alcohol. The alcohol may be used as a mixture of two or more of alcohols, if desired.

Preferably, the alcohol as a substrate is an alcohol represented by the following formula (1), (2) or (3):

(1)

wherein $R^1$ represents a hydrogen atom; a hydrocarbon group which may optionally be substituted with at least one substituent selected from the group consisting of a halogen atom, a nitro group, an alkoxy group, a phenoxy group and an acyloxy group; or a heterocyclic group,

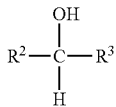
(2)

wherein $R^2$ and $R^3$ represent independently each other a hydrocarbon group which may optionally be substituted with at least one substituent selected from the group consisting of a halogen atom, a nitro group, an alkoxy group, a phenoxy group and an acyloxy group; or a heterocyclic group, while $R^2$ and $R^3$ may be combined to form a ring together with the carbon atom to which they are bonded,

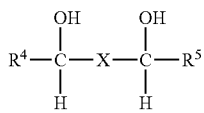
(3)

wherein X represents a single bond or a divalent hydrocarbon group, and $R^4$ and $R^5$ represent independently each other a hydrogen atom; a hydrocarbon group which may optionally be substituted with at least one substituent selected from the group consisting of a halogen atom, a nitro group, an alkoxy group, a phenoxy group and an acyloxy group; or a heterocyclic group, while $R^4$ and $R^5$ may be combined to form a ring together with the carbon atoms to which $R^4$, $R^5$ and X are bonded.

When $R^1$ in the formula (1) is a hydrocarbon group which may optionally be substituted with at least one substituent selected from the group consisting of a halogen atom, a nitro group, an alkoxy group, a phenoxy group and an acyloxy group, the hydrocarbon group is preferably an alkyl group, a cycloalkyl group, an alkenyl group, an aryl group, an arylalkyl group or an arylalkenyl group, each of which has 1 to 20 carbon atoms. The alkoxyl group and the acyloxy group as a substituent of the hydrocarbon group may have 1 to 10 carbon atoms.

When $R^1$ is a heterocyclic group, it preferably has at least one hetero atom selected from oxygen, nitrogen and sulfur atoms. The heterocyclic group is preferably a five- or six-membered ring.

When $R^2$ or $R^3$ in the formula (2) is a hydrocarbon group which may optionally be substituted with at least one substituent selected from the group consisting of a halogen atom, a nitro group, an alkoxy group, a phenoxy group and an acyloxy group, the hydrocarbon group is preferably an alkyl group, a cycloalkyl group, an alkenyl group, an aryl group, an arylalkyl group or an arylalkenyl group, each of which has 1 to 20 carbon atoms. The alkoxyl group and the acyloxy group as a substituent of the hydrocarbon group may have 1 to 10 carbon atoms.

When $R^2$ or $R^3$ is a heterocyclic group, it preferably has at least one hetero atom selected from oxygen, nitrogen and sulfur atoms. The heterocyclic group is preferably a five- or six-membered ring.

When $R^2$ and $R^3$ are combined to form a ring together with the carbon atom to which they are bonded, the ring is preferably a monocyclic or polycyclic ring having 5 to 20 carbon atoms When X in the formula (3) is a divalent hydrocarbon group, it is preferably an alkylidene group, an alkylene group or an arylene group each of which has 1 to 20 carbon atoms.

When $R^4$ or R in the formula (3) is a hydrocarbon group which may optionally be substituted with at least one substituent selected from the group consisting of a halogen atom, a nitro group, an alkoxy group, a phenoxy group and an acyloxy group, the hydrocarbon group is preferably an alkyl group, a cycloalkyl group, an alkenyl group, an aryl group, an arylalkyl group or an arylalkenyl group, each of which has 1 to 20 carbon atoms. The alkoxyl group and the acyloxy group as a substituent of the hydrocarbon group may have 1 to 10 carbon atoms.

When $R^4$ or $R^5$ is a heterocyclic group, it preferably has at least one hetero atom selected from oxygen, nitrogen and sulfur atoms. The heterocyclic group is preferably a five- or six-membered ring.

When $R^4$ and $R^5$ are combined to form a ring together with the carbon atoms to which $R^4$, $R^5$ and X are bonded, the ring is preferably a monocyclic or polycyclic ring having 5 to 20 carbon atoms.

Specific examples of the alcohol represented by the formula (1) include methanol, ethanol, 1-propanol, 1-butanol, 1-pentanol, 1-hexanol, 1-heptanol, 1-octanol, 1-decanol, 1-eicosanol, 3-methyl-1-butanol, 3,3-dimethyl-1-butanol, 4-methyl-1-pentanol, 2-methyl-1-pentanol, 2,2-dimethyl-1-pentanol, 5-methyl-1-hexanol, 3-chloro-1-propanol, allyl alcohol, geraniol, benzyl alcohol, p-methylbenzyl alcohol, p-methoxybenzyl alcohol, p-chlorobenzyl alcohol, p-nitrobenzyl alcohol, 2-phenylethanol, 2-(p-chlorophenyl)ethanol, cinnamyl alcohol, furfuryl alcohol, 2-thiophenemethanol, etc.

Specific examples of the alcohol represented by the formula (2) include 2-propanol, 2-butanol, 2-pentanol, 2-hexanol, 2-heptanol, 2-octanol, 2-decanol, 2-eicosanol, .3-pentanol, 3-hexanol, 3-heptanol, 3-decanol, 3-eicosanol, 4-heptanol, 4-decanol, 4-eicosanol, 3-methyl-2-butanol, 3,3-dimethyl-2-butanol, 4-methyl-2-pentanol, 2-methyl-3-pentanol, 2,2-dimethyl-3-pentanol, 5-methyl-3-hexanol, 1-chloro-2-propanol, 1-bromo-2-propanol, 1-methoxy-2-propanol, 1-phenoxy-2-propanol, 1-acetoxy-2-propanol, 3-penten-2-ol, 1-phenylethanol, cyclopropylphenylmethanol, benzhydrol, 1-(p-tolyl)ethanol, 1-(p-chlorophenyl)ethanol, 1-(p-bromophenyl)ethanol, 1-(p-methoxyphenyl)ethanol, 1-(p-phenoxyphenyl)ethanol, 1-(p-acetoxyphenyl) ethanol, 1-phenyl-2-propanol, 1-(p-tolyl)-2-propanol, 1-(p-chlorophenyl)-2-propanol, 1-(p-bromophenyl)-2-propanol, 1-(p-methoxyphenyl)-2-propanol, 1-(p-phenoxyphenyl)-2-propanol, 1-(p-acetoxyphenyl)-2-propanol, cyclopentanol, cyclohexanol, cycloheptanol, cyclooctanol, cyclododecanol, exo-norborneol, endo-norborneol, 1-indanol, 1-tetralol, 9-fluorenol, etc.

Specific examples of the alcohol represented by the formula (3) include ethylene glycol, propylene glycol, 1,3-propanediol, 1,2-butanediol, 1,3-butanediol, 1,4-butanediol, 2,3-butanediol, 1,2-pentanediol, 1,5-pentanediol, 1,2-hexanediol, 1,6-hexanediol, 1,2-heptanediol, 1,7-heptanediol, 1,2-octanediol, 1,8-octanediol, 1,2-decanediol, 1,10-decanediol, 3-methyl-1,2-butanediol, 3,3-dimethyl-1,2-butanediol, 4-methyl-1,2-pentanediol, 5-methyl-1,2-hexanediol, 3-chloro-1,2-propanediol, 3-butene-1,2-diol, 4-pentene-1,2-diol, 1-phenylethane-1,2-diol, 1-(4-methylphenyl)ethane-1,2-diol, 1-(4-methoxyphenyl)ethane-1,2-diol, 1-(4-chlorophenyl)ethane-1,2-diol, 1-(4-nitrophenyl)ethane-1,2-diol, 1-cyclohexylethane-1,2-diol, 1,2-cyclohexanediol, etc.

Oxygen gas or an air can be used as a molecular oxygen source to be used in the oxidation reaction, and the oxygen gas or air may be diluted with an inert gas such as nitrogen, carbon dioxide, helium, etc.

The contact of the alcohol with molecular oxygen can be carried out by placing a liquid containing the alcohol and the ruthenium-carrying alumina in the atmosphere of a molecular oxygen-containing gas, or by bubbling the molecular oxygen-containing gas through such a liquid.

The oxidation reaction may be carried out in the presence of a solvent, which is less active to the oxidation reaction than alcohol. Examples of such a solvent include halogenated hydrocarbons such as dichloromethane, dichloroethane, chloroform, etc.; esters such as isobutyl acetate, tert-butyl acetate, etc.; nitrites such as acetonitrile, etc.; aromatic hydrocarbons such as toluene, etc.; halogenated aromatic hydrocarbons such as chlorobenzene, trifluorotoluene, etc.; and the like. When the solvent is used, the amount thereof is usually from 1 to 100,000 parts by weight, preferably from 10 to 10,000 parts by weight, per 100 parts by weight of the alcohol.

In the oxidation reaction, a reaction temperature is usually from 20 to 300° C., preferably from 50 to 200° C., and a reaction pressure is usually from 0.1 to 10 MPa. The oxidation reaction may be carried out continuously or batchwise.

The above oxidation reaction produces various carbonyl compounds as oxidation products from the alcohols as the substrates. For example, when the alcohol is a primary alcohol, a corresponding aldehyde and/or carboxylic acid can be produced. When the alcohol is a secondary alcohol, a corresponding ketone can be produced. When the alcohol is a polyhydric alcohol, a corresponding polycarbonyl compound can be produced.

When the alcohol represented by the formula (1) is used, an aldehyde represented by the formula (4):

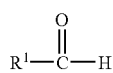

(4)

wherein $R^1$ is the same as defined above, and/or a carboxylic acid represented by the formula (5):

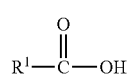

(5)

wherein $R^1$ is the same as defined above, can be produced as an oxidation product.

When the alcohol represented by the formula (2) is used, a ketone represented by the formula (6):

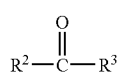

(6)

wherein $R^2$ and $R^3$ are the same as defined above, can be produced as an oxidation product.

When the alcohol represented by the formula (3) is used, a compound represented by the formula (7):

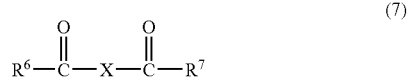

(7)

wherein X is the same as defined above; and $R^6$ represents a hydrogen atom or a hydroxyl group when $R^4$ is a hydrogen atom or $R^6$ is the same as $R^4$ when $R^4$ is a group other than a hydrogen atom; and $R^7$ represents a hydrogen atom or a hydroxyl group when $R^5$ is a hydrogen atom or $R^7$ is the same as $R^5$ when $R^5$ is a group other than a hydrogen atom, can be produced as an oxidation product.

The oxidation product or products can be recovered from the reaction mixture by optionally subjecting the mixture to filtration, concentration, washing, alkali treatment, acid treatment, etc. and then purifying the product or products by distillation, crystallization, etc.

When the ruthenium-carrying alumina prepared by the process of the present invention is used as a catalyst, the alcohols can be oxidized with molecular oxygen at a high conversion. Thus, the oxidation products such as ketones, aldehydes, carboxylic acids, etc. can be produced from the alcohols with a good productivity by such a process.

EXAMPLES

The present invention will be illustrated by the Examples, which do not limit the scope of the invention in any way.

In the Examples, the reaction mixture was analyzed by gas chromatography, and the conversion of a substrate and the selectivity to each product are calculated by the following formulas:

Conversion (%)=(molecular amount of consumed substrate/molecular amount of used substrate)×100

Selectivity (%)=(molecular amount of each product/molecular amount of consumed substrate)×100

PREPARATION OF RUTHENIUM-CARRYING ALUMINA

Examples 1–2 and Comparative Example 1

Example 1

In 60 ml of aqueous solution of ruthenium(III) chloride (8.3 mM), γ-alumina (2.0 g) (Reference catalyst JRC-ALO-4 of the Society of Catalyst, specific surface area: 177 m²/g) was added and suspended, and the suspension was stirred at room temperature for 15 minutes. At this time, the suspension had a pH of 2.1. Thereafter, a 1 M aqueous solution of sodium hydroxide was added to the suspension to adjust pH to 13.2, and then the suspension was stirred at room temperature for 24 hours. The suspension was filtered, and the residual solid was washed with water and dried to obtain a ruthenium-carrying alumina (2.1 g) (ruthenium content: 2.28% by weight, specific surface area: 182 m²/g).

Example 2

In 60 ml of aqueous solution of ruthenium(III) chloride (8.3 mM), γ-alumina (2.0 g) (KHS-24 manufactured by Sumitomo Chemical Co., Ltd., specific surface area: 163 m²/g) was added and suspended, and the suspension was stirred at room temperature for 15 minutes. At this time, the suspension had a pH of 2.3. Thereafter, a 1 M aqueous solution of sodium hydroxide (26.4 ml) was added to the suspension to adjust pH to 13.2, and then the suspension was stirred at room temperature for 24 hours. The suspension was filtrated, and the residual solid was washed with water and dried to obtain a ruthenium-carrying alumina (1.9 g) (ruthenium content: 2.45% by weight, specific surface area: 187 m$^2$/g).

Comparative Example 1

In 60 ml of aqueous solution of ruthenium(III) chloride (8.3 mM), γ-alumina (2.0 g) (Reference catalyst JRC-ALO-4 of the Society of Catalyst, specific surface area: 177 m$^2$/g) was added and suspended, and the suspension was stirred at room temperature for 24 hours. Then, the resulting suspension having a pH of 2.4 was filtrated, and the residual solid was washed with water and dried to obtain a ruthenium-carrying alumina (2.0 g) (ruthenium content: 1.74% by weight, specific surface area: 180 m$^2$/g). Oxidation of Alcohol Examples 3–25 and Comparative Example 2

Example 3

The ruthenium-carrying alumina prepared in Example 1 (0.044 g) was added to and suspended in trifluorotoluene (1.5 ml) and stirred at room temperature for 5 minutes. To the suspension, benzyl alcohol (0.108 g) was added, and oxidized by flowing oxygen through the suspension at 83° C. for 24 hours while stirring. The reaction mixture was analyzed. The conversion of benzyl alcohol was 84%, and the selectivity to benzaldehyde was more than 99%.

Example 4

The ruthenium-carrying alumina prepared in Example 1 (0.11 g) was added to and suspended in trifluorotoluene (1.5 ml) and stirred at room temperature for 5 minutes. To the suspension, benzyl alcohol (0.108 g) was added, and oxidized by flowing oxygen through the suspension at 83° C. for 1 hour while stirring. The reaction mixture was analyzed. The conversion of benzyl alcohol was 99%, and the selectivity to benzaldehyde was more than 99%.

Example 5

The same procedures as in Example 4 were repeated except that air was flowed through the suspension in place of oxygen, and the reaction time was changed to be 4 hours. The conversion of benzyl alcohol was 98%, and the selectivity to benzaldehyde was more than 99%.

Example 6

The same procedures as in Example 4 were repeated except that p-methylbenzyl alcohol was used as a substrate in place of benzyl alcohol. The conversion of p-methylbenzyl alcohol was more than 99%, and the selectivity to p-methylbenzaldehyde was more than 99%.

Example 7

The same procedures as in Example 4 were repeated except that p-methoxybenzyl alcohol was used as a substrate in place of benzyl alcohol. The conversion of p-methoxybenzyl alcohol was more than 99%, and the selectivity to p-methoxybenzaldehyde was more than 99%.

Example 8

The same procedures as in Example 4 were repeated except that p-chlorobenzyl alcohol was used as a substrate in place of benzyl alcohol. The conversion of p-chlorobenzyl alcohol was more than 99%, and the selectivity to p-chlorobenzaldehyde was more than 99%.

Example 9

The same procedures as in Example 4 were repeated except that p-nitrobenzyl alcohol was used as a substrate in place of benzyl alcohol, and the reaction time was changed to be 3 hours. The conversion of p-nitrobenzyl alcohol was 97%, and the selectivity to p-nitrobenzaldehyde was more than 99%.

Example 10

The same procedures as in Example 4 were repeated except that 1-phenylethanol was used as a substrate in place of benzyl alcohol. The conversion of 1-phenylethanol was more than 99%, and the selectivity to acetophenone was more than 99%.

Example 11

The same procedures as in Example 4 were repeated except that cyclopropylphenylmethanol was used as a substrate in place of benzyl alcohol. The conversion of cyclopropylphenylmethanol was more than 99%, and the selectivity to cyclopropylphenylketone was more than 99%.

Example 12

The same procedures as in Example 4 were repeated except that cinnamyl alcohol was used as a substrate in place of benzyl alcohol, and the reaction time was changed to be 1.5 hours. The conversion of cinnamyl alcohol was more than 99%, and the selectivity to cinnamaldehyde was 98%.

Example 13

The same procedures as in Example 4 were repeated except that geraniol was used as a substrate in place of benzyl alcohol, and the reaction time was changed to be 6 hours. The conversion of geraniol was 89%, and the selectivity to geranial was 97%.

Example 14

The same procedures as in Example 4 were repeated except that 2-pentanol was used as a substrate in place of benzyl alcohol, and the reaction time was changed to 5 be hours. The conversion of 2-pentanol was 90%, and the selectivity to 2-pentanone was more than 99%.

Example 15

The same procedures as in Example 4 were repeated except that 2-octanol was used as a substrate in place of benzyl alcohol, and the reaction time was changed to be 2 hours. The conversion of 2-octanol was 91%, and the selectivity to 2-octanone was more than 99%.

Example 16

The same procedures as in Example 4 were repeated except that 2-thiophenemethanol was used as a substrate in place of benzyl alcohol, and the reaction time was changed to be 1.5 hours. The conversion of 2-thiophenemethanol was more than 99%, and the selectivity to 2-thiophenecarboxyaldehyde was more than 99%.

Example 17

The ruthenium-carrying alumina prepared in Example 1 (0.22 g) was added to and suspended in trifluorotoluene (1.5 ml) and stirred at room temperature for 5 minutes. To the suspension, cyclohexanol (0.100 g) was added, and oxidized by flowing oxygen through the suspension at 83° C. for 8 hours while stirring. The reaction mixture was analyzed. The conversion of cyclohexanol was 53%, and the selectivity to cyclohexanone was more than 99%.

Example 18

The same procedures as in Example 17 were repeated except that 3-penten-2-ol was used as a substrate in place of cyclohexanol, and the reaction time was changed to be 6 hours. The conversion of 3-penten-2-ol was 84%, and the selectivity to 3-penten-2-one was more than 99%.

Example 19

The same procedures as in Example 17 were repeated except that 1-octanol was used as a substrate in place of cyclohexanol, and the reaction time was changed to 4 be hours. The conversion of 1-octanol was 80%, and the selectivities to 1-octanal and 1-octanoic acid were 85% and 10%, respectively.

Example 20

The same procedures as in Example 17 were repeated except that cyclopentanol was used as a substrate in place of cyclohexanol. The conversion of cyclopentanol was 92%, and the selectivity to cyclopentanone was more than 99%.

Example 21

The same procedures as in Example 17 were repeated except that cyclooctanol was used as a substrate in place of cyclohexanol, and the reaction temperature was changed to be 6 hours. The conversion of cyclooctanol was 81%, and the selectivity to cycloctanone was more than 99%.

Example 22

The ruthenium-carrying alumina prepared in Example 1 (0.11 g) was added to and suspended in 1-phenylethanol (3.05 g) and stirred at room temperature for 5 minutes. Then, 1-phenylethanol was oxidized by flowing oxygen through the suspension at 150° C. for 18 hours while stirring. The conversion of 1-phenylethanol was 95%, and the selectivity to acetophenone was more than 99%.

Example 23

The ruthenium-carrying alumina prepared in Example 1 (0.11 g) was added to and suspended in 2-octanol (3.25 g) and stirred at room temperature for 5 minutes. Then, 2-octanol was oxidized by flowing oxygen through the suspension at 150° C. for 24 hours while stirring. The conversion of 2-octanol was 98%, and the selectivity to 2-octanone was more than 99%.

Example 24

The ruthenium-carrying alumina prepared in Example 2 (0.11 g) was added to and suspended in trifluorotoluene (1.5 ml) and stirred at room temperature for 5 minutes. To the suspension, benzyl alcohol (0.108 g) was added, and oxidized by flowing oxygen through the suspension at 83° C. for 1 hour while stirring. The reaction mixture was analyzed. The conversion of benzyl alcohol was 99%, and the selectivity to benzaldehyde was more than 99%.

Example 25

The ruthenium-carrying alumina prepared in Example 2 (0.11 g) was added to and suspended in trifluorotoluene (5 ml) and stirred at room temperature for 5 minutes. To the suspension, ethylene glycol (0.071 g) was added, and oxidized by flowing air through the suspension at 83° C. for 5 hours and 10 minutes while stirring. The reaction mixture was analyzed. The conversion of ethylene glycol was 72%, and the selectivity to glyoxal was 91%.

Comparative Example 2

The ruthenium-carrying alumina prepared in Comparative Example 1 (0.044 g) was added to and suspended in trifluorotoluene (1.5 ml) and stirred at room temperature for 5 minutes. To the suspension, benzyl alcohol (0.108 g) was added, and oxidized by flowing oxygen through the suspension at 83° C. for 24 hours while stirring. The reaction mixture was analyzed. The conversion of benzyl alcohol was 23%, and the selectivity to benzaldehyde was more than 99%.

The invention claimed is:

1. A process for oxidizing an alcohol, the process comprising the step of:
   contacting the alcohol with molecular oxygen in the presence of a ruthenium-carrying alumina which is prepared by suspending alumina in a solution containing trivalent ruthenium and adding a base to the suspension.

2. A process for preparing a carbonyl compound, the process comprising the step of:
   oxidizing an alcohol by the process according to claim 1.

3. The process according to claim 2, wherein said alcohol is an alcohol represented by the formula (1):

wherein $R^1$ represents a hydrogen atom; a hydrocarbon group which may optionally be substituted with at least one substituent selected from the group consisting of a halogen atom, a nitro group, an alkoxy group, a phenoxy group and an acyloxy group; or a heterocyclic group, and said carbonyl compound is an aldehyde represented by the formula (4):

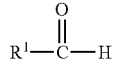
(4)

wherein $R^1$ is the same as defined above, and/or a carboxylic acid represented by the formula (5):

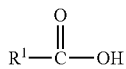
(5)

wherein $R^1$ is the same as defined above.

4. The process according to claim 2, wherein said alcohol is an alcohol represented by the formula (2):

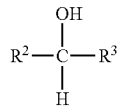
(2)

wherein $R^2$ and $R^3$ represent independently each other a hydrocarbon group which may optionally be substituted with at least one substituent selected from the group consisting of a halogen atom, a nitro group, an alkoxy group, a phenoxy group and an acyloxy group; or a heterocyclic group, while $R^2$ and $R^3$ may be combined to form a ring together with the carbon atom to which they are bonded, and said carbonyl compound is a ketone represented by the formula (6):

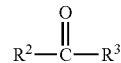
(6)

wherein $R^2$ and $R^3$ are the same as defined above.

5. The process according to claim 2, wherein said alcohol is an alcohol represented by the formula (3):

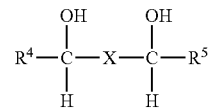
(3)

wherein X is a single bond or a divalent hydrocarbon group, and $R^4$ and $R^5$ represent independently each other a hydrogen atom; a hydrocarbon group which may optionally be substituted with at least one substituent selected from the group consisting of a halogen atom, a nitro group, an alkoxy group, a phenoxy group and an acyloxy group; or a heterocyclic group, while $R^4$ and $R^5$ may be combined to form a ring together with the carbon atoms to which $R^4$, $R^5$ and X are bonded, and said carbonyl compound is a compound represented by the formula (7):

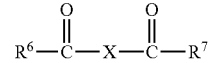
(7)

wherein X is the same as defined above; and $R^6$ represent a hydrogen atom or a hydroxyl group when $R^4$ is a hydrogen atom or $R^6$ is the same as $R^4$ when R is a group other than a hydrogen atom; and $R^7$ represents a hydrogen atom or a hydroxyl group when $R^5$ is a hydrogen atom or $R^7$ is the same as $R^5$ when $R^5$ is a group other than a hydrogen atom.

* * * * *